United States Patent [19]
Morris et al.

[11] Patent Number: 5,585,170
[45] Date of Patent: Dec. 17, 1996

[54] PLACEMENT OF ELECTRIC-FIELD-RESPONSIVE MATERIAL ONTO A SUBSTRATE

[75] Inventors: Marion C. Morris, Appleton; Robert R. Bomber, Green Bay; Franklin M. C. Chen, Appleton; Ronald H. Wideman, Menasha, all of Wis.

[73] Assignee: Kimberly-Clark Corporation, Neenah, Wis.

[21] Appl. No.: 485,950

[22] Filed: Jun. 7, 1995

Related U.S. Application Data

[62] Division of Ser. No. 303,994, Sep. 9, 1994.

[51] Int. Cl.$^6$ ........................................... B32B 27/00
[52] U.S. Cl. .................. 428/286; 148/100; 148/105; 148/108; 428/283; 428/284; 428/323; 428/326; 604/358
[58] Field of Search ........................... 428/283, 284, 428/286, 323, 326; 148/100, 105, 108; 604/358

[56] References Cited

U.S. PATENT DOCUMENTS

| | | | |
|---|---|---|---|
| 2,658,007 | 11/1953 | Cross et al. | 117/17 |
| 2,742,018 | 4/1956 | Lindquist | 118/51 |
| 2,748,018 | 5/1956 | Miller | 117/17 |
| 3,323,933 | 6/1967 | Barford et al. | 117/17 |
| 3,454,347 | 7/1969 | Leimbacher | 8/2 |
| 3,784,395 | 1/1974 | McKown | 117/17 |
| 3,871,328 | 3/1975 | English | 118/629 |
| 3,979,529 | 9/1976 | Rebentisch et al. | 427/25 |
| 4,018,956 | 4/1977 | Casey | 428/86 |
| 4,073,992 | 2/1978 | Lerman et al. | 428/207 |
| 4,096,289 | 6/1978 | Nishwitz et al. | 427/32 |
| 4,297,386 | 10/1981 | Gillette | 427/27 |
| 4,324,198 | 4/1982 | Muz | 118/630 |
| 4,381,728 | 5/1983 | Walling et al. | 118/621 |
| 4,427,712 | 1/1984 | Pan | 427/13 |
| 4,571,351 | 2/1986 | Schaetti | 427/288 |
| 4,689,241 | 8/1987 | Richart et al. | 427/28 |
| 4,908,225 | 3/1990 | Niimura et al. | 427/25 |
| 4,932,352 | 6/1990 | Huvey et al. | 118/202 |
| 5,213,847 | 5/1993 | Hajek | 427/460 |
| 5,492,754 | 2/1996 | Chen | 428/284 |

OTHER PUBLICATIONS

*Electrostatics And Its Applications*, "Nonuniform Field Effects: Dielectrophoresis", pp. 336–362, by Herbert Ackland Pohl, A. D. Moore, Editor, John Wiley & Sons, Apr. 1973.

*Electrostatic Powder Coating*, Dr. J. F. Hughes, Research Studies Ltd., 1984.

*Primary Examiner*—James J. Bell
*Attorney, Agent, or Firm*—John R. Schenian

[57] ABSTRACT

Disclosed is a process using an electric field for contacting a substantially neutrally charged material, that is responsive to an electric field, with a substrate. Also disclosed is a disposable absorbent product, including the electrically responsive material, that is intended for the absorption of body fluids, prepared by the process.

23 Claims, 5 Drawing Sheets

PLACEMENT OF ELECTRIC-FIELD-RESPONSIVE MATERIAL ONTO A SUBSTRATE

This is a divisional application of copending U.S. patent application Ser. No. 08/303,994, filed Sep. 9, 1994, pending.

BACKGROUND OF THE INVENTION

1. Field of the Invention

The present invention relates to a process for preparing an absorbent structure by using an electric field for contacting a substantially neutrally charged material that is responsive to the electric field with a substrate and a disposable absorbent product, intended for the absorption of body fluids, prepared by the process.

2. Description of the Related Art

The use of hydrogel-forming polymeric materials, commonly known as superabsorbents, in disposable absorbent personal care products is known. A wide variety of materials has been described for use as hydrogel-forming polymeric materials in such personal care products. Such materials include natural-based materials such as agar, pectin, gums, carboxyalkyl starch, and carboxyalkyl cellulose; as well as synthetic materials such as polyacrylates, polyacrylamides, and hydrolyzed polyacrylonitrile.

Such superabsorbent materials are generally employed in absorbent products such as diapers, training pants, adult incontinence products, and feminine care products in order to increase the absorbent capacity of such products while reducing their overall bulk. Such superabsorbent materials are generally present in absorbent products in a fibrous matrix, such as a matrix of wood pulp fluff. A matrix of wood pulp fluff generally has an absorbent capacity of about 6 grams of liquid per gram of fluff. The superabsorbent materials described above generally have an absorbent capacity of at least about 10, preferably of about 20, and often of up to 50 times their weight of liquid. Clearly, incorporation of such superabsorbent materials in personal care products can reduce the overall bulk while increasing the absorbent capacity of such products.

Adhesive materials are also well known for use in disposable absorbent products. The adhesive material is typically used in the form of extruded lines, beads, or looping swirls of hot-molt adhesive to adhere different elements of the disposable absorbent product together. For example, a topsheet may be adhered to a backsheet, or a hydrogel-forming polymeric material may be constrained into a desired pattern by applying the hydrogel-forming polymeric material to adhesive material. A wide variety of materials has been described for use as adhesive materials in personal care products. Such materials include hot-melt adhesives, pressure-sensitive adhesives, or the like.

Various methods of incorporating a hydrogel-forming polymeric material or an adhesive material into a personal care product are known. One such method includes using a vacuum process to prepare a layered absorbent structure comprising a tissue web base and a hydrogel-forming polymeric material layer ideally located between two wood pulp fluff layers. A tissue web base moves over a continuous belt former, under vacuum, which attracts the desired wood pulp fluff and hydrogel-forming polymeric material from a forming chamber. In practice, however, turbulent air flow in the forming chamber typically results in an absorbent structure without a clear-cut layered structure wherein the hydrogel-forming polymeric material is somewhat randomly distributed within and across the wood pulp fluff layers.

Another vacuum process may be used to form an absorbent structure wherein the hydrogel-forming polymeric material is distributed within a porous tissue web base. Again, a tissue web base moves over a vacuum drum former which attracts the desired hydrogel-forming polymeric material from a forming chamber. The porosity of the tissue web base permits the absorbent material to become distributed within the tissue web base. However, the pore size distribution of the tissue web base typically overlaps the particle size distribution of the hydrogel-forming polymeric material particles. As such, an amount of the hydrogel-forming polymeric material will not be distributed within the tissue web base and will generally result in airborne hydrogel-forming polymeric material particles as the absorbent structure is further processed.

Another method of incorporating a hydrogel-forming polymeric material into a personal care product includes using a gravimetric process wherein the hydrogel-forming polymeric material is gravimetrically applied to a moving tissue web base with adhesive lines applied on the surface of the tissue web base. Typically, an amount of the hydrogel-forming polymeric material does not contact the adhesive lines so that such hydrogel-forming polymeric material is not adhered onto the tissue web base.

Known processes for incorporating a hydrogel-forming polymeric material or an adhesive material into a disposable absorbent product typically result in placement of an amount of the hydrogel-forming polymeric material or the adhesive material in undesired locations within the personal care product. Such an inefficient placement of the hydrogel-forming polymeric material or the adhesive material generally results in the use of more of the hydrogel-forming polymeric material or the adhesive material than would ideally be needed, thereby increasing the costs of manufacturing the personal care product. Additionally, the presence of the hydrogel-forming polymeric material or the adhesive material in undesired locations within the personal care product may negatively affect the designed performance of the personal care product. Furthermore, the inefficient placement of the hydrogel-forming polymeric material or the adhesive material often results in airborne hydrogel-forming polymeric material or adhesive material particles which can create housekeeping or cleanliness problems.

SUMMARY OF THE INVENTION

The present invention concerns an efficient and effective manner for incorporating a material responsive to an electric field, such as a hydrogel-forming polymeric material or an adhesive material, into a absorbent structure useful for the absorption of liquids, such as body liquids, wherein the placement of the material responsive to an electric field within the absorbent structure may be substantially controlled.

One aspect of the present invention concerns a process for incorporating a material responsive to an electric field into an absorbent structure, wherein the material responsive to an electric field remains substantially neutrally charged during the process.

One embodiment of such a process comprises using an electric field to contact a material responsive to an electric field, selected from the group consisting of a hydrogel-forming polymeric material and an adhesive material, with a substrate, wherein the material responsive to an electric field remains substantially neutrally charged during the process.

In another aspect, the present invention concerns a disposable absorbent product comprising an absorbent structure prepared by the process disclosed herein.

One embodiment of such a disposable absorbent product comprises a liquid-permeable topsheet, a backsheet attached to the liquid-permeable topsheet, and an absorbent structure positioned between the topsheet and the backsheet. The absorbent structure is prepared by a process comprising using an electric field to contact a material responsive to an electric field, selected from the group consisting of a hydrogel-forming polymeric material and an adhesive material, with a substrate, wherein the material responsive to an electric field remains substantially neutrally charged during the process.

DETAILED DESCRIPTION OF THE PREFERRED EMBODIMENTS

It has been discovered that, by using a material that is responsive to an electric field, wherein the material remains substantially neutrally charged when in the presence of the electric field, it is possible to take advantage of the electric-field-responsive property of the material in order to effectively and efficiently incorporate the material into a disposable absorbent structure or product.

By using a material responsive to an electric field, it is possible to use an electric field to selectively locate the material onto a substrate or within a disposable absorbent structure or product. It will be recognized, however, that it is generally desirable that the final disposable absorbent structure or product exhibits substantially no permanent electric field under the conditions under which the final disposable absorbent structure or product will be used. It is desirable, therefore, that the material responsive to an electric field only be responsive when subjected to an electric field, yet remains substantially unresponsive when the electric field is absent.

As used herein, a "material responsive to an electric field" or an "electric-field-responsive material", or similar terms, is meant to refer to a material of which a substantially neutrally charged sample exhibits translational motion when in the presence of a generally nonuniform electric field. Suitably, the material responsive to an electric field used in the present invention is selected from the group consisting of a hydrogel-forming polymeric material or an adhesive material.

As used herein, "hydrogel-forming polymeric material" is meant to refer to a high absorbency material commonly referred to as a superabsorbent material. Such high absorbency materials are generally capable of absorbing an amount of a liquid, such as synthetic urine, a 0.9 weight percent aqueous saline solution, or bodily fluids, such as menses, urine, or blood, at least about 10, suitably about 20, and up to about 50 times the weight of the superabsorbent material at the conditions under which the superabsorbent material is being used. Typical conditions include, for example, a temperature of between about 0° C. to about 100° C. and suitably ambient conditions, such as about 23° C. and about 30 to about 60 percent relative humidity. Upon absorption of the liquid, the superabsorbent material typically swells and forms a hydrogel.

The superabsorbent material may be formed from an organic hydrogel material which may include natural materials, such as agar, pectin, and guar gum, as well as synthetic materials, such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyridines. Other suitable hydrogel polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble yet water swellable. Crosslinking may, for example, be by irradiation or covalent, ionic, van der Weals, or hydrogen bonding. Suitable superabsorbent materials are typically available from various commercial vendors, such as The Dow Chemical Company, Hoechst Celanese, Allied Colloids Limited, or Stockhausen, Inc.

The hydrogel-forming polymeric material, employed in the absorbent structures or products of the present invention, suitably should be able to absorb a liquid under an applied load. For the purposes of this application, the ability of a hydrogel-forming polymeric material to absorb a liquid under an applied load, and thereby perform work, is quantified as the Absorbency Under Load (AUL) value. The AUL value is expressed as the amount (in grams) of an aqueous 0.9 weight percent sodium chloride solution which the hydrogel-forming polymeric material can absorb in about 60 minutes per gram of hydrogel-forming polymeric material under a load of about 0.3 pound per square inch (approximately 2.0 kilopascals) while restrained from swelling in the plane normal to the applied load. The hydrogel-forming polymeric material employed in the absorbent structures of the present invention suitably exhibit an AUL value of at least about 15, more suitably of at least about 20, and up to about 50 grams of liquid per gram of hydrogel-forming polymeric material. The method by which the AUL value may be determined is set forth, for example, in detail in U.S. Pat. No. 5,149,335 or U.S. Pat. No. 5,247,072, incorporated herein by reference.

Suitably, the hydrogel-forming polymeric material is in the form of particles which, in the unswollen state, have maximum cross-sectional diameters within the range of from about 50 micrometers to about 1000 micrometers, preferably within the range of from about 100 micrometers to about 800 micrometers, as determined by sieve analysis according to American Society for Testing and Materials (ASTM) test method D-1921. It is to be understood that the particles of hydrogel-forming polymeric material falling within the ranges described above may comprise solid particles, porous particles, or may be agglomerated particles comprising many smaller particles agglomerated into particles falling within the described size ranges.

The hydrogel-forming polymeric material is typically present in an absorbent structure or product of the present invention in an amount effective to result in the absorbent structure or product being able to absorb a desired amount of liquid. The hydrogel-forming polymeric material is beneficially present in an absorbent structure in an amount of from about 1 to about 99 weight percent, suitably in an amount of from about 5 to about 95 weight percent, and more suitably of from about 10 to about 90 weight percent, based on the total weight of the hydrogel-forming polymeric material and substrate in the absorbent structure.

Adhesive materials are also well known for use in disposable absorbent products. A wide variety of materials has been described for use as adhesive materials in disposable absorbent products. Adhesives useful in the present invention may be of any known type, such as a thermoplastic hot-melt adhesive, a reactive adhesive, or the like. An example of a thermoplastic hot-melt adhesive includes a synthetic rubber-based adhesive based on polystyrene-polybutadiene-polystyrene chemistry and a tackifier based on hydrocarbon chemistry, available from the National Starch and Chemical Corporation under the trade designation NS 34-5541. A description of compositions of hot-melt adhesives can be found, for example, in "CRC Elastomer Technology Handbook", edited by Nicholas P. Cheremisinoff (CRC Press, 1993), Chapter 24, incorporated herein by reference.

Examples of reactive adhesives include crosslinked amine-epoxide compounds or moisture-cured polyurethanes. The chemistry of such reactive adhesives is known to those skilled in the art and may be found, for example, in "Contemporary Polymer Chemistry", by Harry Alcock and Frederick Lampe (Prentice Hall, 1990), incorporated herein by reference.

Suitably, the adhesive material is in the form of particles which have maximum cross-sectional diameters within the range of from about 50 micrometers to about 1000 micrometers, preferably within the range of from about 100 micrometers to about 800 micrometers, as determined by sieve analysis according to American Society for Testing and Materials (ASTM) test method D-1921. It is understood that the particles of adhesive material falling within the ranges described above may comprise solid particles, porous particles, or may be agglomerated particles comprising many smaller particles agglomerated into particles falling within the described size ranges.

The adhesive material may be contacted with a substrate in either a tacky or a nontacky state. If the adhesive material is contacted with a substrate in a nontacky state, then the adhesive material may be further treated so as to make the adhesive material tacky and suitable for use as an adhesive. For example, nontacky particles of a thermoplastic, hot-melt adhesive material may be first contacted with a substrate by using an electric field as described herein and then the adhesive material is subsequently treated, such as by being subjected to heat, so as to make the adhesive material tacky and thus useful as an adhesive.

For example, powdered adhesives based upon ethylene, vinyl acetate, polyesters, or polyamides are generally nontacky at typical room temperatures. Thus, such powdered adhesives may be easily applied to a substrate in a nontacky condition using an electric field as described herein and then the powdered adhesive is subsequently treated, such as by being subjected to heat with a nip roll, so as to make the powdered adhesive tacky and thus useful as an adhesive.

The adhesive material is typically present in an absorbent structure or product of the present invention in an amount effective to result in the absorbent structure or product being joined or adhered together with other components or materials of the absorbent structure or product in a desired manner. The adhesive material is beneficially present in an absorbent structure in an amount of from greater than 0 to about 99 weight percent, suitably in an amount of from about 1 to about 50 weight percent, and more suitably of from about 1 to about 25 weight percent, based on the total weight of the adhesive material and substrate in the absorbent structure.

The hydrogel-forming polymeric material and the adhesive material may generally be used individually, or together, or mixed or combined with other materials in any acceptable manner as long as the hydrogel-forming polymeric material exhibits its desired absorbent properties, the adhesive material exhibits its desired adhesive properties, and both the hydrogel-forming polymeric material and the adhesive material exhibit the desired electric-field-responsive properties described herein. For example, a hydrogel-forming polymeric material and an adhesive material may be mixed together and used in a process as a single composition such that the hydrogel-forming polymeric material adheres to a substrate to which the composition is contacted. Other methods of mixing or combining the hydrogel-forming polymeric material, the adhesive material, or other materials will be readily apparent to those skilled in the art.

In one embodiment of the present invention, the process comprises first contacting the substrate with an adhesive material and subsequently using an electric field to contact a hydrogel-forming polymeric material with the adhesive material on the substrate, wherein the hydrogel-forming polymeric material remains substantially neutrally charged during the process.

In another embodiment of the present invention, the process comprises using an electric field to first contact the substrate with a hydrogel-forming polymeric material, wherein the hydrogel-forming polymeric material remains substantially neutrally charged during the process and, subsequently, contacting the hydrogel-forming polymeric material with an adhesive material.

The hydrogel-forming polymeric material and the adhesive material according to the present invention are suited for use in disposable absorbent products such as diapers, adult incontinent products, and bed pads; in catamenial devices such as sanitary napkins, and tampons; and in other absorbent products such as wipes, bibs, wound dressings, and surgical capes or drapes. Accordingly, in another aspect, the present invention relates to a disposable absorbent product comprising the material responsive to an electric field as described herein.

Use of a hydrogel-forming polymeric material in disposable absorbent products allows for the formation of a disposable absorbent product which is able to rapidly receive a discharged liquid and yet which product is thin. Typically, the hydrogel-forming polymeric material will be incorporated into a disposable absorbent product in the form of an absorbent structure. Such disposable absorbent products generally comprise a liquid-permeable topsheet, a backsheet attached to the topsheet, and an absorbent structure, such as an absorbent structure comprising a substrate and a hydrogel-forming polymeric material of the present invention, positioned between the topsheet and backsheet.

As used herein, the term "substrate" is meant to refer to a material with which the material responsive to an electric field is contacted by using a process employing an electric field. Materials suitable for use as a substrate will be well known to those skilled in the art. Typical substrates can include a fibrous matrix or a film.

The substrate may be in the form of a single, integrally-formed layer or of a composite comprising multiple layers. If the substrate comprises multiple layers, the layers are preferably in liquid communication with one another such that a liquid present in one layer can flow or be transported to another layer. For example, the layers may be separated by cellulosic tissue wrap sheets known to those skilled in the art.

The material responsive to an electric field may be distributed in or on the substrate in a generally uniform manner or may be present in or on the substrate as a layer or other nonuniform distribution, such as in a desired pattern.

When the substrate comprises a single, integrally-formed layer, the concentration of material responsive to an electric field may increase along the thickness of the substrate in a gradual, nonstepwise fashion or in a more stepwise fashion. Similarly, the density may decrease through the thickness of the substrate in a nonstepwise manner or in a stepwise manner.

The substrate is beneficially present in an absorbent structure of the present invention in an amount of from about 1 to about 99 weight percent, suitably from about 5 to about 95 weight percent, and more suitably from about 10 to about 90 weight percent, based on the total weight of the material responsive to an electric field and substrate in the absorbent structure.

A wide variety of natural and synthetic fibers can be employed in the preparation of a fibrous matrix useful in the present invention. Illustrative fibers include, but are not limited to, wood and wood products, such as wood pulp fibers, cellulose or cellulose acetate flocs, cotton linter flocs and the like, inorganic fibers, synthetic fibers such as nylon flocs, rayon flocs, polyacrylonitrile fibers, and the like.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

It is also possible to use mixtures of one or more natural fibers, or one or more synthetic fibers, or combinations of the two. Preferred fibers are those which are wettable in nature. However, nonwettable fibers can also be used. It is possible to treat the fiber surfaces by an appropriate method to render them more or less wettable. When surface-treated fibers are employed, the surface treatment is desirably nonfugitive; that is, the surface treatment desirably does not wash off the surface of the fiber with the first liquid insult or contact. For the purposes of this application, a surface treatment on a generally nonwettable polymer will be considered to be nonfugitive when a majority of the fibers demonstrate a liquid in air contact angle of less than 90° for three consecutive contact angle measurements, with drying between each measurement. That is, the same fiber is subjected to three separate contact angle determinations and, if all three of the contact angle determinations indicate a contact angle of liquid in air of less than 90°, the surface treatment on the fiber will be considered to be nonfugitive. If the surface treatment is fugitive, the surface treatment will tend to wash off of the fiber during the first contact angle measurement, thus, exposing the nonwettable surface of the underlying fiber, and will demonstrate subsequent contact angle measurements greater than 90°. Beneficial wettability agents include polyalkylene glycols, such as polyethylene glycols. The wettability agent is used in an amount comprising beneficially less than about 5 weight percent, suitably less than about 3 weight percent, and more suitably less than about 2 weight percent, of the total weight of the fiber, material, or absorbent structure being treated.

As used herein, the term "wettable" is meant to refer to a fiber or material which exhibits a liquid-in-air contact angle of less than 90°, wherein the liquid contacting the fiber or material is a liquid such as water, synthetic urine, urine, menses, blood, or a 0.9 weight percent aqueous saline solution. The contact angle may be determined, for example, by methods known to those skilled in the art. Suitably, a wettable fiber refers to a fiber which exhibits a 0.9 weight percent aqueous saline solution in air contact angle of less than 90°, at a temperature between about 0° C. and about 100° C., and suitably at ambient conditions, such as about 23° C.

Fibrous matrixes for incorporation into an absorbent structure are generally well known. A fibrous matrix may take the form of, for example, a batt of comminuted wood pulp fluff, a tissue layer, a hydroentangled pulp sheet, a mechanically softened pulp sheet, or of a web structure comprising an entangled fibrous mass formed, for example, from an extruded thermoplastic composition. Suitably, the fibrous matrix is formed so as to constrain or entrap the material responsive to an electric field within, or onto, its structure. The material responsive to an electric field may be incorporated into or onto the fibrous matrix either during or after the formation of the general form of the fibrous matrix.

Suitably, the fibrous matrix has a basis weight ranging from about 0.025 grams per square meter of fibrous matrix material to about 400 grams per square meter of fibrous matrix material.

Suitably, the fibrous matrix has a density ranging from about 0.05 grams per cubic centimeter of fibrous matrix material to about 0.5 grams per cubic centimeter of fibrous matrix material.

Suitably, the fibers comprising the fibrous matrix have a fiber length ranging from about 0.1 centimeter to about 3.0 centimeters.

A fibrous matrix useful in the present invention may be formed by an air-laying process, a spunbond or meltblown process, a carding process, a wet-laid process, or by essentially any other process known to those skilled in the art for forming a fibrous matrix.

If the substrate is in the form of a spunbonded material, materials suitable for use as the substrate include spunbonded polypropylene or polyethylene having a basis weight of from about 15 to about 25 grams per square meter.

If the substrate is in the form of a film material, materials suitable for use as the substrate include polyolefin films. Other materials suitable for use as a film material will be known to those skilled in the art.

In one embodiment of the present invention, a disposable absorbent product is provided, which disposable absorbent product comprises a liquid-permeable topsheet, a backsheet attached to the liquid-permeable topsheet, and an absorbent structure positioned between the liquid-permeable topsheet and the backsheet, wherein the absorbent structure is prepared by a process comprising using an electric field to contact a material responsive to an electric field, selected from the group consisting of a hydrogel-forming polymeric material and an adhesive material, with a substrate, wherein the material responsive to an electric field remains substantially neutrally charged during the process.

While one embodiment of the invention will be described in terms of the use of a substantially neutrally charged hydrogel-forming polymeric material that is responsive to an electric field in an infant diaper, it is to be understood that such a hydrogel-forming polymeric material is equally suited for use in other disposable absorbent products known to those skilled in the art.

Exemplary disposable absorbent products are generally described in U.S. Pat. No. 4,710,187; U.S. Pat. No. 4,762,521; U.S. Pat. No. 4,770,656; U.S. Pat. No. 4,798,603; and U.S. Ser. No. 08/096,654, filed Jul. 22, 1993 in the name of Hansen et al., which references are incorporated herein by reference.

Figure 1:
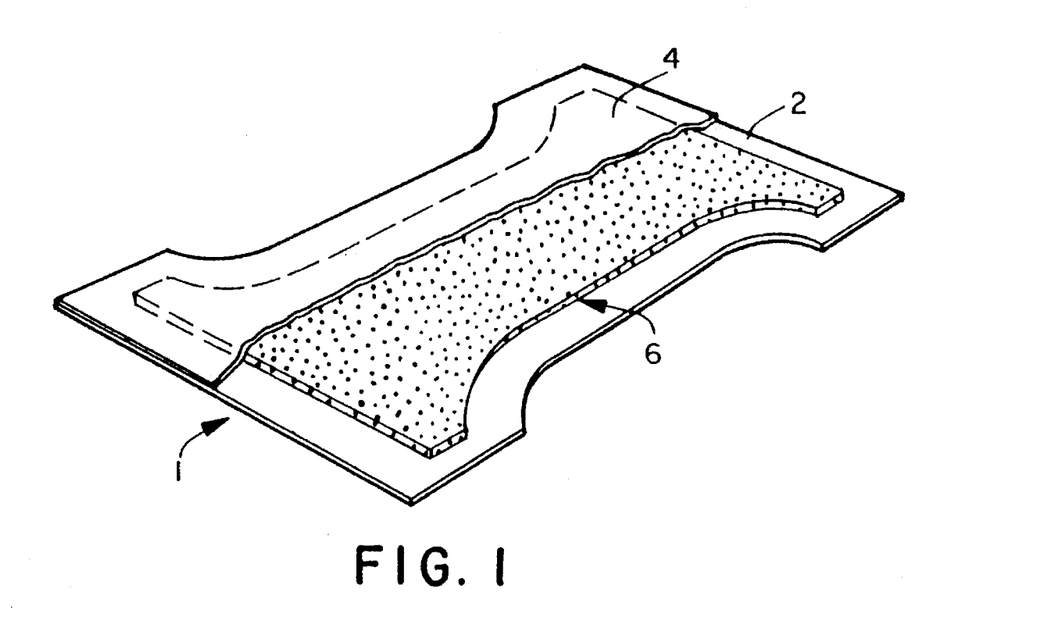
FIG. 1 represents a disposable diaper according to the present invention.

Turning now to the drawings, FIG. 1 illustrates a disposable diaper 1 according to one embodiment of the present invention. Disposable diaper 1 includes a backsheet 2, a topsheet 4, and an absorbent structure 6, located between the backsheet 2, and the topsheet 4. Absorbent structure 6 is an absorbent structure according to the present invention. Specifically, in the illustrated embodiment, absorbent structure 6 is prepared using a process comprising using an electric field to contact a hydrogel-forming polymeric material responsive to an electric field with a substrate, wherein the hydrogel-forming polymeric material remains substantially neutrally charged during the process.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

Various methods may be used to incorporate an electric-field responsive material into an absorbent structure or disposable absorbent product by using an electric field. In the present invention, it is desired that the electric-field-responsive material remain substantially neutrally charged when in the presence of an electric field during the process. That is to say, the electric-field-responsive material does not substantially possess a net charge, either positive or negative, when in the presence of an electric field. Ideally, each particle of the electric-field-responsive material is neutrally charged. However, as will be appreciated by those skilled in the art, stray or air-borne electrical charges may result in an insubstantial number of particles of the electric-field-responsive material becoming electrically charged.

Even though substantially neutrally charged, the electric-field-responsive material is affected by an electric field. This is believed to be because individual particles of the substantially neutrally charged, electric-field-responsive material generally become polarized so as to form a dipole within each individual particle of the material when in the presence of an electric field. The translational motion of a substantially neutrally charged material caused by polarization effects in a nonuniform electric field is generally referred to as dielectrophoresis. In contrast, the response of a charged material in an electric field is generally referred to as electrophoresis. Thus, in the present invention, it is desired that any movement by the substantially neutrally charged electric-field-responsive material when in a nonuniform electric field be the result of dielectrophoresis and not electrophoresis. A discussion of dielectrophoresis and electrophoresis may be found, for example, in Chapter 14 of "Electrostatics and Its Applications", A. D. Moore, editor, (April, 1973), John Wiley & Sons, incorporated herein by reference.

Typically, in the present invention, an electric field will be generated between an electric field source and a collecting means. Suitably, the collecting means is grounded. Alternatively, the collecting means may be electrically charged, generally with the opposite electrical charge as that of the electric field source. The substantially neutrally charged, electric-field-responsive material is introduced into the electric field in such a way as to be attracted towards the collecting means. If a substrate is positioned on the collecting means, the electric-field-responsive material may be contacted directly with the substrate. Alternatively, the electric-field-responsive material may be contacted directly with the collecting means and subsequently transferred to a substrate.

Since the electric-field-responsive material is to remain substantially neutrally charged during the process of the present invention, the electric-field-responsive material should generally be introduced into the electric field in the space between the electric field source and the collecting means closer to the collecting means than to the electric field source so as to be attracted towards the collecting means. This is because the substantially neutrally charged, electric-field-responsive material will generally be attracted towards the region of highest electric field intensity. As such, if the substantially neutrally charged, electric-field-responsive material is introduced into the space between the electric field source and the collecting means too close to the electric field source, the substantially neutrally charged, electric-field-responsive material may be undesirably attracted towards the electric field source.

The electric field source is typically provided with a voltage potential which creates an electric field between the electric field source and a collecting means. The electric field source may generally be operated with either direct current or alternating current. In one embodiment of the present invention, the electric field source will be in the form of an electrostatic electrode, such as an electrostatic bar, an electrostatic wire, an electrostatic generator, or the like.

The collecting means as used herein may take many forms as, for example, a roll, a conveyor belt, a drum former, or the like. Generally, a desired pattern of conductive material is created on the surface of the collecting means to which the electrical-field-responsive material is to be attracted. The rest of the collecting means will generally be nonconductive so that a dipole is formed only where the conductive material exists. Thus, for example, as a nonconductive substrate is passed over the collecting means, the substrate takes on an electrostatic charge only where the pattern of conductive material on the collecting means exists to which the electric-field-responsive material is to be attracted. Suitably, the collecting means comprises a magnet or magnets for enhancing the ability of the collecting means to attract and retain the material responsive to an electric field. Suitably, such a collecting means comprising a magnet or magnets is used when the material responsive to an electric field is in a composition also comprising a magnetically responsive material.

The present invention can be employed to produce selected mixtures and distributions of an electric-field-responsive material into or onto a substrate during an airlaying or airforming operation. However, other mixtures of materials may be produced employing the present invention depending on the particular parameters desired in an absorbent structure. Such alternative configurations and uses are contemplated as being within the scope of the present invention.

Figure 2:
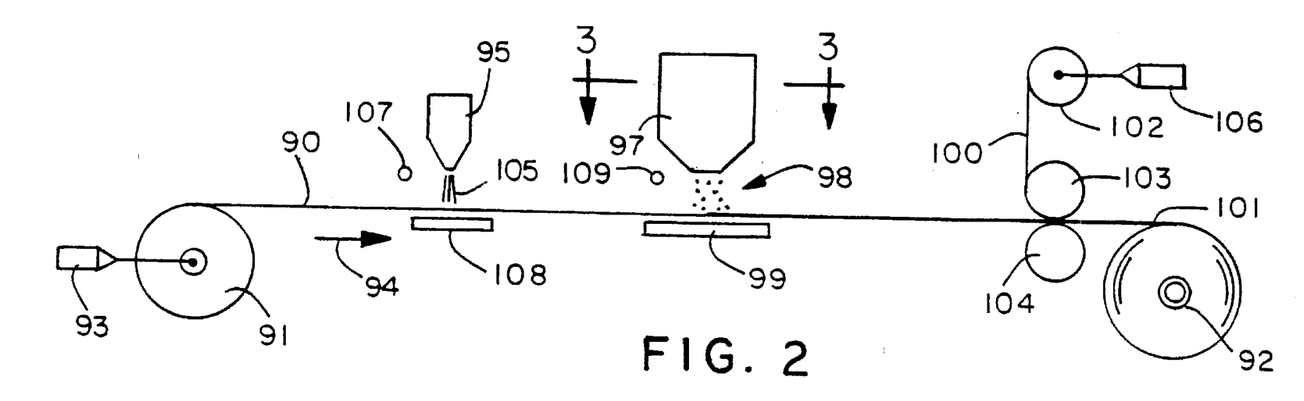
FIG. 2 illustrates a schematic view of a representative apparatus useful in the present invention.
Figure 3:
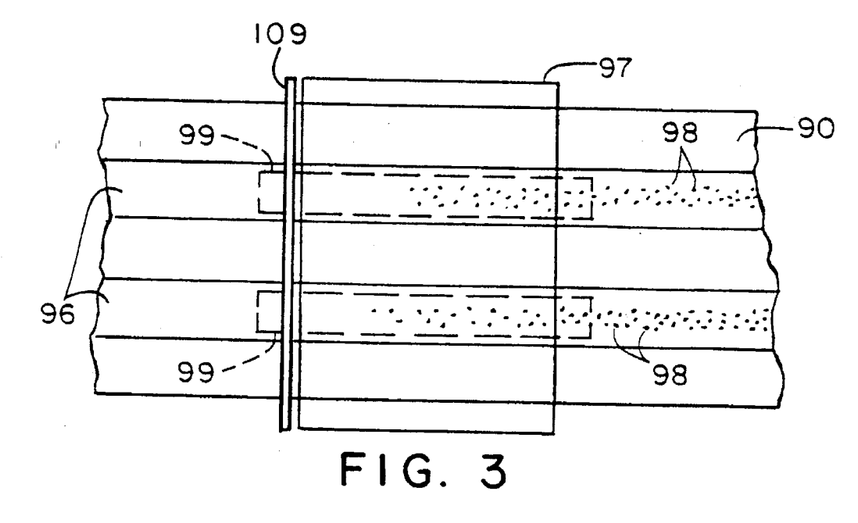
FIG. 3 illustrates a cross-sectional, top plan view of the hydrogel-forming polymeric material delivery means taken along line 3—3 of FIG. 2.

Referring now to FIGS. 2 and 3 to describe a method for incorporating a hydrogel-forming polymeric material and an adhesive material into an absorbent structure, substrate support layer 90 travels from support roller 91 to collector roller 92. A suitable driving means, such as electric motor 93, is operably connected to move substrate support layer 90 at a selected speed along movement direction 94. As substrate support layer 90 travels underneath adhesive applicator means 95, adhesive 105 is gravimetrically applied to substrate support layer 90 to form adhesive lines 96. A first electric field source 107 is positioned near the outlet of the adhesive applicator means 95 to provide an electric field 120 that affects the adhesive 105. A first collecting means 108 is located beneath substrate support layer 90, in the general location of adhesive applicator means 95, to direct the positioning of the adhesive 105 onto the substrate support layer 90.

As substrate support layer 90 travels underneath hydrogel-forming polymeric material delivery means 97, hydrogel-forming polymeric material particles 98 are gravimetrically applied in the general location of the adhesive lines 96. A second electric field source 109 is positioned near the outlet of the hydrogel-forming polymeric material delivery means 97 to provide an electric field 121 that affects the hydrogel-forming polymeric material particles 98. A second collecting means 99 is located beneath substrate support layer 90, in the general location of hydrogel-forming polymeric material delivery means 97, to direct the positioning of the hydrogel-forming polymeric material particles 98 onto the adhesive lines 96 on substrate support layer 90.

A substrate top layer 100 is then layered onto substrate support layer 90, thereby sandwiching the hydrogel-forming polymeric material particles 98 between the substrate layers to form absorbent structure 101 which is collected on collector roller 92. Substrate top layer 100 travels from support roller 102 and is contacted with substrate support layer 90 between nip rollers 103 and 104. A suitable driving means, such as electric motor 106, is operably connected to move substrate top layer 100 at a selected speed from support roller 102 into contact with substrate support layer 90.

It has been found that the conditions under which the process of the present invention is performed may have an effect on the efficiency of the process. For example, it is desirable that the electric field source and the collecting means have as small of a current as possible running between them. Furthermore, it is desirable that the electric field source not be maintained at such a high voltage potential as to cause corona discharges from the electric field source. Both a current and a corona discharge generally represent the migration of electrons into the air between the electric field source and the collecting means. Such migrating electrons typically create gas ions which may attach themselves to the electric-field-responsive material introduced into the electric field and give such electric-field-responsive materials an electrical charge.

The electric field source should generally be maintained at a voltage potential beneficially between about 2 to about 10 kilovolts per centimeter of space between the electric field source and the collecting means. A voltage potential less than about 2 kilovolts per centimeter of space between the electric field source and the collecting means may not be sufficient to provide a strong enough electric field to effectively drive the material responsive to the electric field towards the collecting means. A voltage potential greater than about 10 kilovolts per centimeter of space between the electric field source and the collecting means may result in corona discharges from the electric field source.

It is desirable that the electric field source and the collecting means have no current running between them. However, a current of between about 0.1 to about 0.2 milliamps between the electric field source and the collecting means, over a distance of about 6 inches, has typically been found to not substantially interfere with the desired operation and effectiveness of the process of the present invention. Beneficially, the current running between the electric field source and the collecting means will be less than about 1 milliamp.

The use of substantially neutrally charged, electric-field-responsive material has been found to provide the advantage of being able to form multi-layers of the electric-field-responsive material on the collecting means. Although substantially neutrally charged, the electric-field-responsive material is polarized in the presence of the electric field so that oppositely charged portions of neighboring particles on the collecting means can be attracted to each other. As such, it is possible to observe the formation of strings or chains of individual particles of the electric-field-responsive material on the collecting means. In contrast, if the electric-field-responsive material is charged in the presence of the electric field, neighboring particles on the collecting means will tend to be repelled from each other since they are similarly charged, thereby making the formation of multi-layers difficult.

Furthermore, the use of a process wherein the electric-field-responsive material remains substantially neutrally charged when in the presence of an electric field has been found to generally provide a higher deposition level of the electric-field-responsive material onto the collecting means in high humidity environments. In contrast, when the electric-field-responsive material is substantially charged when in the presence of an electric field, a high humidity environment generally tends to dissipate the charge on the electric-field-responsive material so that the effectiveness of such a process is affected. A high humidity environment would typically be a humidity above about 50 percent.

In addition, the use of a process wherein the electric-field-responsive material remains substantially neutrally charged when in the presence of an electric field generally is believed to provide one with greater flexibility and simplicity in regards to the process equipment and setup used. For example, one may generally use either an alternating current or a direct current electric field source when the electricfield-responsive material remains substantially neutrally charged during the process. This is because the substantially neutrally charged, electric-field-responsive material will generally behave similarly in electric fields generated by either alternating current or direct current electric field sources. In contrast, when the electric-field-responsive material is substantially charged when in the presence of an electric field, the use of an alternating current electric field source will generally have no effect in placing a substantially charged, electric-field-responsive material onto a substrate.

It has been found that, when using an electric field to transfer an electric-field-responsive material to a substrate, treatment of or modification of the electric-field-responsive material may affect the efficiency with which the electric-field-responsive material is transferred to the substrate. For example, the electric-field-responsive material may be mixed or combined with a magnetically responsive material or put into solution with various solvents and then dried and recovered to enhance the electric field responsiveness of the electric-field-responsive material. It has been found that the deposition rate of an electric-field-responsive material, such as of a hydrogel-forming polymeric material, in the process of the present invention may be generally dependent on the dielectric constant, volume resistivity, particle size, and/or the moisture content of the electric-field-responsive material. For example, in general, a greater deposition rate of the electric-field-responsive material may be achieved with higher dielectric constant, lower volume resistivity and/or higher moisture content of the electric-field-responsive material. The electric-field-responsive material should generally exhibit a dielectric constant that is beneficially at least about 3, suitably at least about 5, more suitably at least about 7, and up to about 20, when measured after about 1 second after being initially charged by a voltage source of about 250 volts. The electric-field-responsive material should generally exhibit a volume resistivity of beneficially at least about $0.01 \times 10^{-12}$ ohm·centimeters and suitably at least about $0.05 \times 10^{-12}$ ohm·centimeters. The electric-field-responsive material has a moisture content of beneficially less than about 5 weight percent, suitably less than about 3 weight percent, and more suitably less than about 1 weight percent, based on the total weight of the electric-field-responsive material.

As such, as used herein, a "magnetically responsive material" is generally meant to refer to a material selected from the group consisting of ferrimagnetic materials and superparamagnetic materials.

A ferrimagnetic material is a material in which the magnetic moments of neighboring domains tend to align antiparallel to each other, but the moments are of different magnitudes. This is in contrast, for example, to a ferromagnetic material wherein the magnetic moments of neighboring domains tend to align in a common direction. Examples of ferrimagnetic materials include maghemite (gamma $Fe_2O_3$), magnetite ($Fe_3O_4$), and ferrite. Ferrite is a compound having the chemical formula $XFe_2O_4$, wherein X represents a divalent metal, such as iron or zinc, whose size is such that it will fit into the structure of the crystal. Ferrimagnetic materials may be commercially purchased as, for example, from Miles, Inc., Pittsburgh, Pa., USA, or prepared in situ.

Suitably, the magnetically responsive material such as a ferrimagnetic material has a coercivity of less than about 400 gauss (about 0.04 weber/square meter) and a remanence induction of less than about 2500 gauss (about 0.25 weber/square meter). Coercivity is the force required to demagnetize a material or, in other words, the amount of applied magnetic field that is required to overcome the magnetic induction of a material and bring its residual magnetism back to zero. Remanence is the residual magnetic flux density that remains in a material after the removal of an applied magnetic field.

A superparamagnetic material is a material comprising fine particles in which the fine particles behave substantially independently of one another when a magnetic field is absent but, when placed in a magnetic field, are magnetized parallel to the magnetic field to an extent proportional to the magnetic field. An example of a superparamagnetic material is nanocrystals of gamma $Fe_2O_3$. Superparamagnetic materials may be purchased, for example, from Advanced Magnetics, Cambridge, Mass., USA, or may be prepared in situ. Suitably, the superparamagnetic materials have a coercivity of about 0 gauss and a remanence induction of about 0 gauss.

TEST PROCEDURES

Measurement of Volume Resistivity

Figure 4:
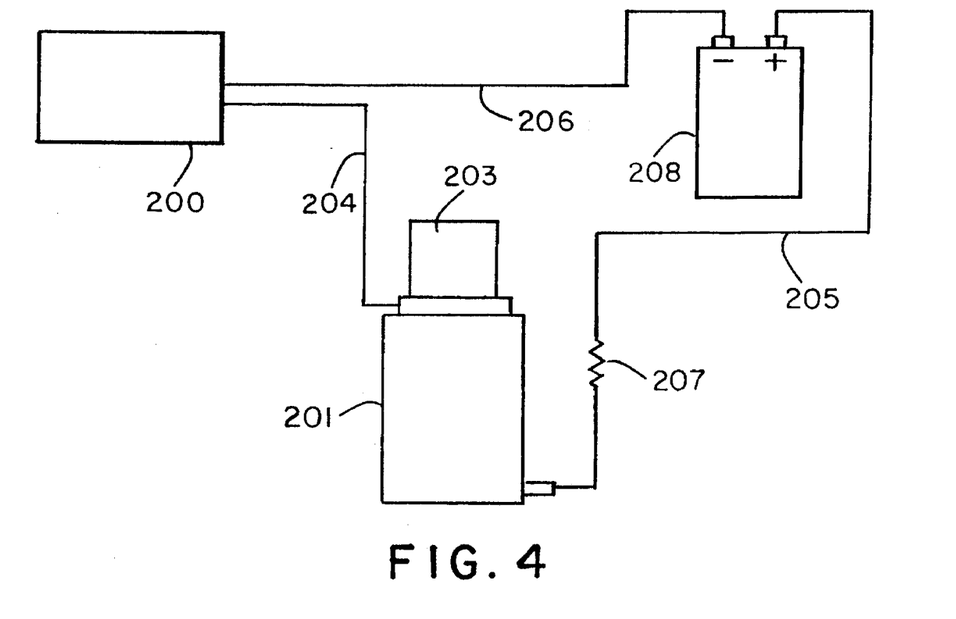
FIG. 4 illustrates a schematic view of a representative apparatus useful in measuring the volume resistivity of a material.

Referring to FIG. 4, the electrometer 200 is turned on and allowed to warm up for about 2 hours in order to obtain its rated accuracy. The current mode of the electrometer 200 is selected. A resistivity tube 201, comprising a teflon tube with a brass bottom and having a radius of about 3.0 centimeters and a height of about 7.07 centimeters, is cleaned with alcohol or other suitable solvent to remove all foreign materials and fingerprints. The resistivity tube 201 is filled with the material to be tested. The resistivity tube 201 should be filled the same way for each test for consistent measurement accuracy. For example, the resistivity tube 201 may be filled with test material and then gently tapped a few times to encourage settling of the test material. The test material is leveled even with the top rim of the resistivity tube 201 by using a straight edge. The test material is covered with a brass plate 202 and then a 1 kilogram mass 203 is placed on top of the brass plate 202 to help ensure consistent compaction of the test material. The bottom of the brass plate 202 should be even with the top of the resistivity tube 201. Wires 204, 205, and 206 are then connected between electrometer 200, brass plate 202, resistivity tube 201, 22 mega-ohm resistor 207, and 300 volt battery 208 as shown in FIG. 20. The electrometer 200 is put into the autorange mode and the zero checking is disabled. The electrometer 200 is then read and the current recorded. The volume resistivity may then be calculated using the formula:

Volume Resistivity=4×(Voltage)/(Current) ohm·centimeters,
wherein the voltage is measured in volts and the current is measured in amps.

If the test material is too resistive, it will generally be characterized by low current measurements which, depending on the sensitivity of the electrometer, may result in erratic current readings. Such erratic current readings will generally be due to stray currents or noise present in the environment which will typically be difficult to eliminate. Any test materials that exhibit this behavior may be classified as an insulator (or nonconductive) and treated likewise.

At the other extreme are test materials which are too conductive and will thus be characterized by high current flows. At current flows greater than about 130 nano-amps, the 22 mego-ohm resistor used to protect the 300 volt battery begins to introduce an error greater than about 1 percent. To eliminate this error, one may replace the 22 mega-ohm resistor with a wire containing a lower valued resistor (for example, about 10 kilo-ohm) or eliminate the resistor completely. If this is done, however, caution must be exercised to avoid grounding the high voltage wire, or damage to the battery can result. Any test materials that exhibit this behavior may be classified as conductive and treated likewise.

Measurement of Dielectric Constant

Figure 5:
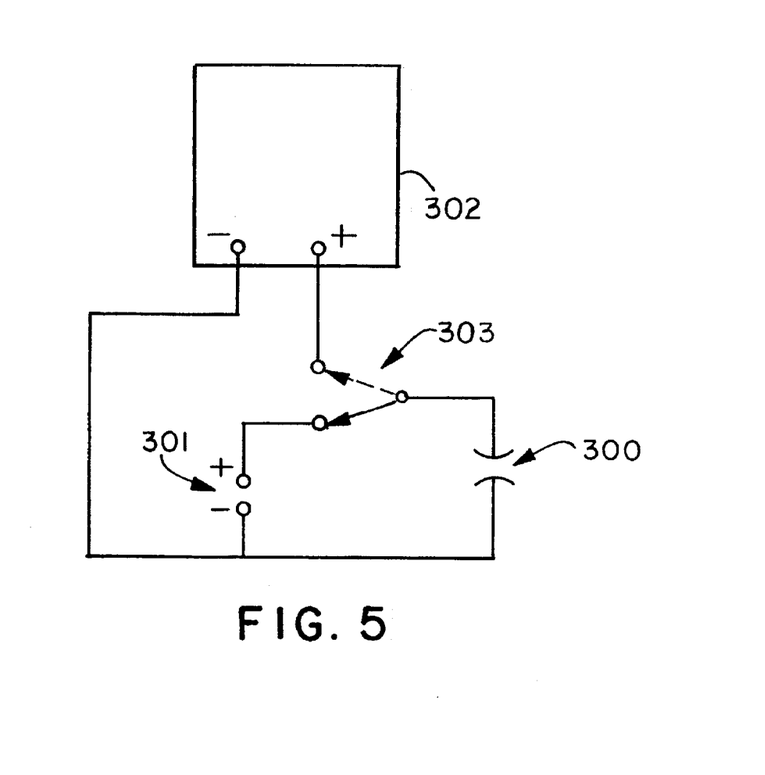
FIG. 5 illustrates a schematic view of a representative apparatus useful in measuring the dielectric constant of a material.

Referring to FIG. 5, a test material is placed in a capacitor 300 which is initially charged by a voltage source 301 of about 250 volts. The capacitor 300 is then disconnected from the voltage source 301 and connected to an electrometer 302 by use of switch 303. The electrometer 302 measures the charge in the capacitor 300. Two measurements are taken using the electrometer 302. First, the immediate reading given when the capacitor 300 is connected to the electrometer 302 is referred to as the instantaneous measurement. Second, the reading given one second after the capacitor 300 is connected to the electrometer 302 is referred to as the one-second measurement. The test material is removed from the capacitor 300 and a similar procedure is used to measure the coulomb value when only air is present in the capacitor 300. The measured coulomb value is then converted into the dielectric constant of the test material by taking the ratio of the coulomb value when the test material is present in the capacitor to the coulomb value when air is present in the capacitor. Dielectric constant values are calculated using both the instantaneous and the one-second measurements. The instantaneous dielectric constant value is referred to herein as D(inst). The one-second dielectric constant value is referred to herein as D(1 sec).

EXAMPLE 1

Figure 6:
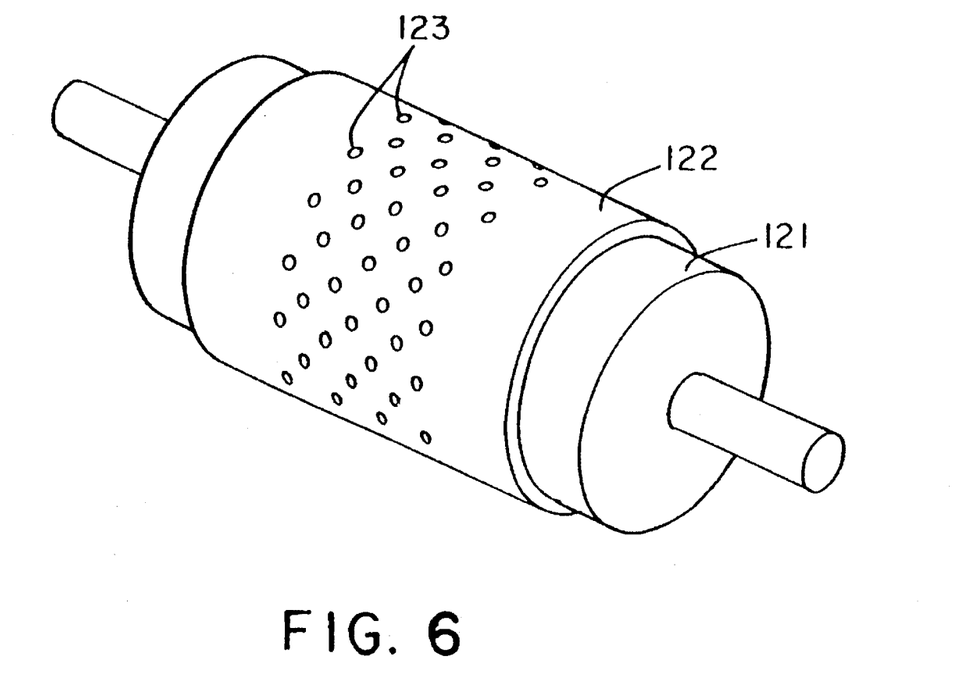
FIG. 6 illustrates a conductive roll collecting means useful in the present invention.
Figure 7:
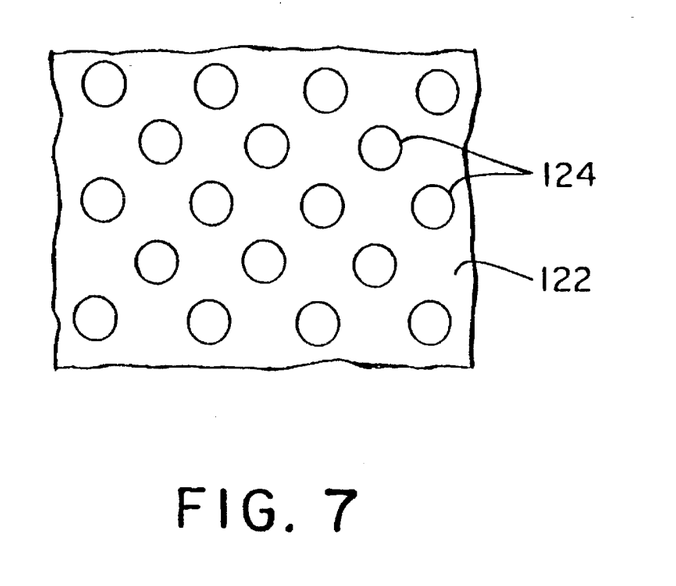
FIG. 7 illustrates a pattern for placing a conductive material in the conductive roll collecting means as illustrated in FIG. 6.

Referring to FIGS. 6 and 7, a conductive roll collecting means to selectively place an electrically responsive material using an electric field was made from a 4-inch diameter steel roll 121 and a 4-inch diameter polyvinylchloride pipe 122. The polyvinylchloride pipe 122 was drilled to accept 0.375 inch diameter circular pieces of a conductive metal 123 according to a pattern as shown in FIG. 7 and slid onto the steel roll 121. From center to center, in a row or column, the metal pieces 123 were placed about 1.0134 inches apart, such that there were fourteen of the metal pieces 123 in a row around the circumference of the polyvinylchloride pipe 122. The prepared roll is used in a setup similar to that shown in FIG. 8.

A process using an electric field was employed to selectively locate a hydrogel-forming polymeric material onto a fibrous matrix substrate.

Figure 8:
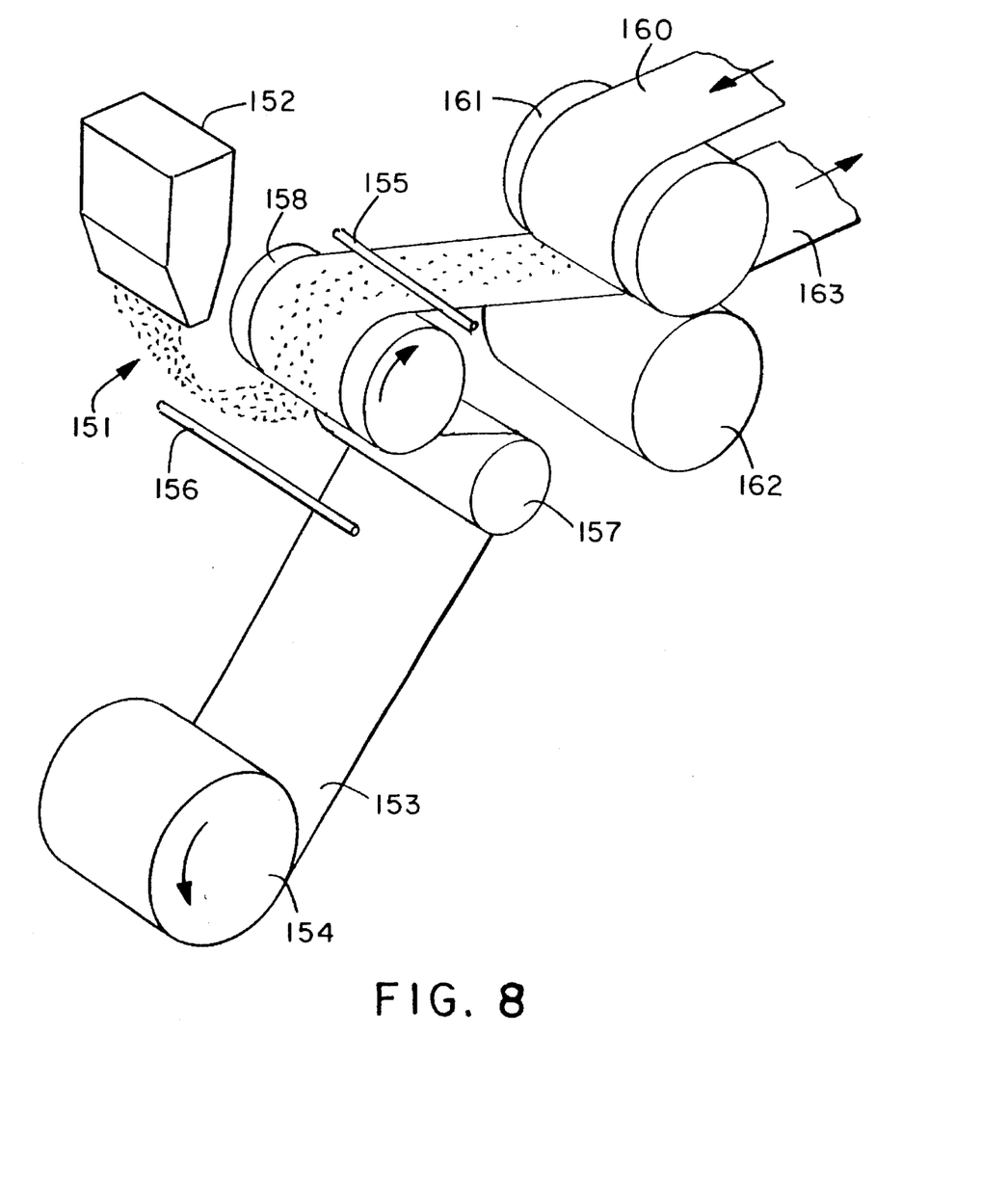
FIG. 8 illustrates a schematic view of a representative apparatus useful in the present invention.

Referring to FIG. 8, a hydrogel-forming polymeric material 151 (a polyacrylate superabsorbent, available from the Hoechst Celanese Corporation under the trade designation IM 3900) was placed in a hydrogel-forming polymeric material delivery means 152. A blue tissue substrate 153, having a cross section width of about 4 inches and a basis weight of about 0.5 ounce per square yard, was unwound from a substrate roll 154, passing over an idler roll 157. The blue tissue substrate 153 then passed over a collecting means conductive roll 158, as shown in FIG. 6, which was grounded. The hydrogel-forming polymeric material 151 was gravimetrically discharged from the delivery means 152 to fall to a location closer to the conductive roll 158 than to an electric field source. The electric field source, such as an electrostatic generator 156, with a direct current voltage of about 16 kilovolts, was used to direct the falling hydrogel-forming polymeric material 151 towards the tissue substrate 153 wherein the hydrogel-forming polymeric material 151 was attracted by the grounded conductive roll 158 into the pattern shown. The electric field source was located a distance of about 1.5 to about 1.75 inches away from the grounded conductive roll 158. The electrostatic generator 156 created an electrical field in the air from the electrostatic generator 156 across to the collecting means conductive roll 158. The grounded conductive roll 158 provided an opposite charge to that provided by the electrostatic generator 156 and the hydrogel-forming polymeric material particles 151 accelerated towards the conductive roll 158. An antistatic bar 155 was located near where the substrate 153 left the conductive roll 158 to remove any electrostatic charges from the blue tissue substrate 153.

An adhesive coated, hydroentangled pulp web 160, having a basis weight of about 1.75 ounces per square yard, was then layered onto the blue tissue substrate 153, and the combination passed through a set of nip rolls 161 and 162. The final product was an absorbent laminate structure 163.

A sample of the final product was weighed to determine the amount of hydrogel-forming polymeric material placed onto the blue tissue substrate. A 4-foot sample of the blue tissue substrate weighed about 8 grams and a 4-foot sample of the adhesive-sprayed hydroentangled pulp substrate weighed about 24 grams, such that a 4-foot sample of the combined substrate weighed about 32 grams. A 4-foot sample of the final absorbent laminate structure was prepared and weighed about 56 grams. As such, about 6 grams of hydrogel-forming polymeric material was placed per linear foot of substrate.

EXAMPLE 2

Different treatment or preparation methods of hydrogel-forming polymeric materials were used to study the effect on deposition rates of the hydrogel-forming polymeric material onto a substrate when using an electric field.

Sample 67-1: About 950 grams of the fraction passing through a 20 mesh screen and captured on a 100 mesh screen (particle sizes of between about 150 to about 850 micrometers) of a granular, partial sodium salt of crosslinked polyacrylic acid (commercially available from The Dow Chemical Company under the trade designation DRYTECH 2024) was allowed to equilibrate to ambient conditions of about 50 percent relative humidity and about 72° F. (about 22° C.). The material was then dried for two hours at 150° C. in a convection oven.

Sample 67-2: About 950 grams of DRYTECH 2024 were sieved as for Sample 67-1 and then dried overnight in a vacuum oven set at a pressure of about 27 inches of mercury and at 92° C.

Sample 67-3: About 1000 grams of DRYTECH 2024 was swelled in about 5 liters of distilled water, spread into pans, and then dried at about 70° C. in a convection oven for about 3 days. The dried material was ground in a blender and sieved so as to retain the fraction passing through a 20 mesh screen and captured on a 100 mesh screen.

Sample 67-4: About 250 grams of DRYTECH 2024 was swelled with about 94 grams of concentrated hydrochloric acid in about 2406 grams of distilled water. The proportions of DRYTECH 2024, hydrochloric acid, and water were calculated to change the DRYTECH 2024 from about 75 percent neutralized (sodium acrylate moieties) to about 35 percent neutralized. The acidified gel was allowed to stand for about 15 minutes and was then mixed with about 1 liter of anhydrous methanol to collapse the gel and extract the sodium chloride resulting from the acidification procedure.

The gel was collected on a filter, dried at about 70° C. in a convection oven, and sieved so as to retain the fraction passing through a 20 mesh screen and captured on a 100 mesh screen.

Sample 67-5: About 1000 grams of DRYTECH 2024 were sieved as for Sample 67-1 and then slurried in about 1.5 liters of anhydrous methanol and treated with about 47 grams of concentrated hydrochloric acid for about 30 minutes. The DRYTECH 2024 was filtered from the methanol and dried in a 70° C. convection oven.

Sample 67-6: About 953 grams of DRYTECH 2024 were sieved as for Sample 67-1 and then slurried in about 1250 milliliters of anhydrous methanol and treated with about 9.5 grams of a nonionic surfactant (commercially available from BASF Wyandotte Corporation under the trade designation TETRONIC 908) dissolved in about 200 grams of methanol for about 1 hour. The DRYTECH 2024 was filtered from the methanol and dried in a 70° C. convection oven.

Sample 67-7: About 950 grams of DRYTECH 2024 were sieved as for Sample 67-1 and then extracted with about 1250 milliliters of a 3 to 1 volume ratio of methanol to water for about one hour. The DRYTECH 2024 was then dried in a 70° C. convection oven.

Sample 68-1: About 952 grams of DRYTECH 2024 were sieved as for Sample 67-1 and then stirred in about 1500 milliliters of a 3 to 1 volume ratio of methanol to water containing about 9.5 grams of a polyethylene oxide (commercially available from Union Carbide Corporation under the trade designation E-8000) for about one hour. The DRYTECH 2024 was recovered by filtration and dried in a 70° C. convection oven.

Sample 68-2: DRYTECH 2024 right out of its container was sieved and only the fraction having particle sizes greater than about 600 micrometers was used as is.

Sample 68-3: DRYTECH 2024 right out of its container was sieved and only the fraction having particle sizes between about 300 to about 600 micrometers was used as is.

Sample 68-4: DRYTECH 2024 right out of its container was sieved and only the fraction having particle sizes smaller than about 300 micrometers was used as is.

Sample 68-5: An experimental bead polymer having a high surface area by virtue of a wrinkled particle shape (available from The Dow Chemical Company under the designation SHARPEI) was used as received.

Sample 66-8: This sample was a composite of seven batches of magnetically enhanced, 75 percent neutralized poly(acrylic acid) superabsorbent material. Three of the batches were prepared at a 1 molar scale and four batches were prepared at a 2 molar scale (based on acrylic acid monomer). Although there were slight differences in the procedures used to prepare each batch, a representative procedure for preparing a two-molar batch is as follows:

The reactor was a 1000 milliliter resin flask equipped with a paddle stirrer, a thermocouple, and a reflux condenser. The reactor was charged with 60 grams of sodium hydroxide and 473 grams of water. After the sodium hydroxide had dissolved, 3.08 grams of a crosslinking agent, N,N'-methylenebisacrylamide, was rinsed into the reactor with 100 grams of water. Ferric oxide ($Fe_3O_4$), in an amount of 1.82 grams, was then slurried into the reactor in 20 grams of water. The reactor was purged with nitrogen for about 30 minutes while being heated to about 70°–75° C. An initiator solution of 1 gram of sodium persulfate in 20 grams of water was added to the reactor. The reactor contents then gelled, usually within about 10 minutes. The gel was then allowed to sit for about an hour so as to complete the polymerization. The gel was then removed from the reactor, cut into about one-half inch pieces and dried in a convection oven overnight at about 125° C. The dry pieces of polymer were chopped in a laboratory blender and sieved. The fraction having a size between about 140 to about 850 micrometers was collected.

The samples were tested for dielectric constant and volume resistivity using the test procedures described herein. The testing for the volume resistivity was done in triplicate, with the results averaged, over two days. The conditions in the laboratory were about the same for both days with the temperature at about 71° F. (about 22° C.) and the relative humidity at about 54 percent. The samples were also tested for moisture content by measuring the weight loss of a sample by heating the sample for about two hours at about 150° C.

The samples were then used in the process described in Example 1 to determine the deposition level of the hydrogel-forming polymeric material samples onto an absorbent substrate as measured by the grams of sample material deposited per linear foot of the absorbent substrate. The results of these various evaluations are shown in Table 1.

TABLE 1

| Sample No. | Sample Deposit Level (grams/foot) | Dielectric Constant D(inst) | Dielectric Constant D(1 sec) | Volume Resistivity (ohm centimeters $\times 10^{-12}$) | Moisture Content (weight %) |
|---|---|---|---|---|---|
| 66-8 | 11.56 | 11.07 | 13.72 | 1.7 | — |
| 68-5 | 8.22 | 8.48 | 14.01 | 0.06 | 4.0 |
| 67-3 | 7.71 | 6.96 | 7.56 | 4.1 | 3.5 |
| 67-7 | 6.78 | 5.45 | 6.87 | 4.1 | 1.2 |
| 68-4 | 5.32 | 4.63 | 7.13 | 3.7 | 1.1 |
| 67-4 | 4.65 | 5.98 | 6.39 | 26.0 | 4.6 |
| 68-1 | 3.83 | 5.21 | 7.10 | 4.3 | 1.4 |
| 67-6 | 3.74 | 3.68 | 5.72 | 30.0 | 0.4 |
| 68-3 | 3.74 | 4.30 | 6.46 | 2.6 | 0.5 |
| 67-5 | 1.95 | 2.90 | 4.19 | 9900.0 | 1.0 |
| 67-2 | 1.79 | 3.30 | 4.62 | 290.0 | 0.2 |
| 68-2 | 1.60 | 4.38 | 6.00 | 3.6 | 0.4 |
| 67-1 | 0.94 | 15.58 | 18.20 | 0.0043 | 3.0 |

The data in Table 1 indicates a good correlation between the deposition level of the samples and the dielectric constant values of the samples, except for two samples. First, Sample 67-1 exhibited an unusually low electrical resistance (or, alternatively, a high conductivity). It is normally difficult to electrostatically charge a highly conductive material for electric field deposition onto an absorbent substrate. Second, Sample 68-5 comprises an unusually shaped material which, when combined with the low volume resistivity (high conductivity) and high dielectric constant of the material, may affect its comparison with the other test materials. The data in Table 1 also indicates some correlation between the deposition level of the samples and the volume resistivity of the sample (generally the lower the better) and the particle size of the sample (generally the smaller the better).

EXAMPLE 3

The effect of using a direct current and an alternating current electric field source was investigated.

A brass shim stock plate was used as a collection means. The brass shim stock plate was positioned vertically and was grounded. An electrostatic bar with discharge points, connected to an electric generator, was used as the electric field source. The electrostatic bar was positioned vertically about 1.75 inches away from the brass shim stock plate. Particles of hydrogel-forming polymeric material (Hoechst Celanese IM 3900 polyacrylate superabsorbent) were dropped in the space between the brass shim stock plate and the electrostatic bar, slightly nearer to the brass shim stock plate than to the electrostatic bar.

In a first instance, the electric generator was a direct current source with a voltage potential of about 20 kilovolts. In a second instance, the electric generator was an alternating current source with a voltage potential of about 10 kilovolts. In both instances, the hydrogel-forming polymeric material was attracted to the ground brass shim stock plate collecting means.

As an additional test, a cellulose triacetate shim stock plastic mask, having dimensions similar to that of the brass shim stock plate, was made up with a pattern of holes through it so as to only expose the brass shim stock plate where the holes existed. Again, alternately using both a direct current and an alternating current electric field source, the plastic mask was placed over the brass shim stock plate. Under the influence of the electric fields, the plastic mask was observed to move to and cling to the brass shim stock plate. In the case of using the direct current electric field source, the voltage was reduced to about 15 to about 18 kilovolts so as to prevent arcing between the electric field source and the brass shim stock plate.

When the hydrogel-forming polymeric material particles were dropped in the space between the brass shim stock plate/plastic mask and the electrostatic bar, the hydrogel-forming polymeric material particles were attracted substantially only to the brass shim stock plate through the plastic mask holes. Over time, the hydrogel-forming polymeric material particles formed a multi-layer in excess of the depth of the plastic mask. When the electric field sources were turned off and the plastic mask carefully removed from the brass shim stock plate, the hydrogel-forming polymeric material particles were observed to largely remain in the pattern of the holes on the brass shim stock plate. Although the use of either the direct current or the alternating current electric field source resulted in an effective amount of the hydrogel-forming polymeric material particles making contact with the brass shim stock plate, a slightly larger buildup of the hydrogel-forming polymeric material was observed when the direct current electric field source was used. When using the direct current electric field source, a current of about 0.1 milliamp was measured. When using the alternating current electric field source, no current measurement was made.

It is believed that this example shows that the hydrogel-forming polymeric material remained substantially neutrally charged when in the presence of the electric field. Particularly in the instances where the alternating current electric field source was used, if the hydrogel-forming polymeric material had been electrically charged, it is believed that the hydrogel-forming polymeric material would not have been attracted towards either the brass shim stock plate or the electrostatic bar.

EXAMPLE 4

The use of a nonconducting, polyethylene film substrate was compared to the use of a conducting, tissue substrate.

A setup and procedure similar to that used in Example 1 was used. The operating conditions were as follows. A hydrogel-forming polymeric material (Hoechst Celanese IM 3900 polyacrylate superabsorbent) was delivered from a hopper delivery means at a rate of about 115 grams of material per minute. The electric field source was operated at about 20 kilovolts. The relative humidity in the room was about 40 percent and the temperature was at about 74° F. (about 22° C.). The substrates were fed through the system at a rate of about 10 feet per minute.

In a first instance, a tissue web with a basis weight of about 2.1 grams per foot, and a width of about 11.5 inches was used as the bottom substrate. The top substrate layer was a hydroentangled pulp with applied adhesive with a basis weight of about 5.94 grams per foot and a width of about 11.5 inches. A one-foot sample of the final product was measured to have a total weight of about 11.7 grams, such that about 3.66 grams of the hydrogel-forming polymeric material was placed onto the tissue substrate.

In a second instance, a polyethylene film with a basis weight of about 1.5 grams per foot, and a width of about 8.5 inches was used as the bottom substrate. The top substrate layer was a hydroentangled pulp with an applied adhesive with a basis weight of about 4.54 grams per foot and a width of about 8.5 inches. A one-foot sample of the final product was measured to have a total weight of about 11.8 grams, such that about 5.76 grams of the hydrogel-forming polymeric material was placed onto the polyethylene film substrate.

Because the polyethylene film is a substantially nonconducting material, it would be expected that, if the hydrogel-forming polymeric material was substantially electrically charged when in the electric field, then such an electrically charged hydrogel-forming polymeric material would not be substantially placed onto the polyethylene film, since the polyethylene could not dissipate the electrical charges from the hydrogel-forming polymeric material. As such, particles of the electrically charged hydrogel-forming polymeric material would tend to repel each other and not build up onto the polyethylene film. However, as shown here, an additional 57 weight percent of the hydrogel-forming polymeric material was observed to be placed onto the polyethylene film as compared onto the tissue web under similar conditions. This is believed to indicate that the hydrogel-forming polymeric material remains substantially neutrally charged when in the presence of the electric field.

EXAMPLE 5

The use of polystyrene as a material responsive to an electric field was compared to the use of a hydrogel-forming polymeric material.

A setup and procedure similar to that used in Example 1 was used. The operating conditions were as follows. The particular material responsive to an electric field was delivered from a hopper delivery means at a rate of about 180 grams of material per minute. The electric field source was operated at about 18 kilovolts. The relative humidity in the room was about 45 to 50 percent and the temperature was at about 74° F. (about 22° C.). A tissue web substrate, with a basis weight of about 2.1 grams per foot, was fed through the system at a rate of about 25 feet per minute. The top substrate layer was a hydroentangled pulp with an applied adhesive with a basis weight of about 5.94 grams per foot and a width of about 11.5 inches.

In a first instance, a polystyrene material was used as the material responsive to an electric field. A one-foot sample of the final product was measured to have a total weight of about 10.8 grams, such that about 2.76 grams of the polystyrene material was placed onto the tissue substrate.

In a second instance, a hydrogel-forming polymeric material, a granular, partial sodium salt of crosslinked polyacrylic acid (commercially available from Stockhausen, Inc. under the trade designation FAVOR 870) was used as the material responsive to an electric field. A one-foot sample of the final product was measured to have a total weight of about 10.2 grams, such that about 2.16 grams of the hydrogel-forming polymeric material was placed onto the tissue substrate.

Because the polystyrene material is an amorphous material, it is believed that the polystyrene material cannot hold a permanent electrical charge. As such, it is believed that, since a substantial amount of the polystyrene material was transferred to the tissue substrate, the polystyrene material must be affected by the electric field even though the polystyrene material is substantially neutrally charged.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A disposable absorbent product comprising a liquid-permeable topsheet, a backsheet attached to the liquid-permeable topsheet, and an absorbent structure positioned between the liquid-permeable topsheet and the backsheet, wherein the absorbent structure is prepared by a process comprising using an electric field to contact a material responsive to an electric field, selected from the group consisting of a hydrogel-forming polymeric material and an adhesive material, with a substrate, wherein the material responsive to an electric field remains substantially neutrally charged during the process.

2. The disposable absorbent product of claim 1 wherein the material responsive to an electric field is a hydrogel-forming polymeric material.

3. The disposable absorbent product of claim 1 wherein the hydrogel-forming polymeric material is selected from the group consisting of agar, pectin, and guar gum, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyridines.

4. The disposable absorbent product of claim 3 wherein the hydrogel-forming polymeric material is selected from the group consisting of carboxymethyl cellulose and alkali metal salts of polyacrylic acid.

5. The disposable absorbent product of claim 2 wherein the hydrogel-forming polymeric material is present in the absorbent structure in an amount of from about 1 to about 99 weight percent, based on the total weight of the hydrogel-forming polymeric material and the substrate in the absorbent structure.

6. The disposable absorbent product of claim 1 wherein the material responsive to an electric field is an adhesive material.

7. The disposable absorbent product of claim 6 wherein the adhesive material is selected from the group consisting of thermoplastic hot-melt adhesives and reactive adhesives.

8. The disposable absorbent product of claim 7 wherein the adhesive material is selected from the group consisting of synthetic rubber-based adhesives based on polystyrene-polybutadiene-polystyrene chemistry, crosslinked amine-epoxide compounds, and moisture cured polyurethanes.

9. The disposable absorbent product of claim 6 wherein the adhesive material is present in the absorbent structure in an amount of from greater than 0 to about 99 weight percent, based on the total weight of the adhesive material and the substrate in the absorbent structure.

10. The disposable absorbent product of claim 1 wherein the substrate comprises a fibrous matrix or a film.

11. The disposable absorbent product of claim 10 wherein the fibrous matrix comprises fibers selected from the group consisting of wood pulp, cellulose, cellulose acetate, cotton linter, nylon, rayon, and polyacrylonitrile fibers.

12. The disposable absorbent product of claim 10 wherein the fibrous matrix is in the form selected from the group consisting of a batt of comminuted wood pulp fluff, a tissue layer, a hydroentangled pulp sheet, a mechanically softened pulp sheet, and a web structure.

13. The disposable absorbent product of claim 1 wherein the material responsive to an electric field is in the form of particles which have maximum cross-sectional diameters within the range of from about 50 micrometers to about 1000 micrometers.

14. The disposable absorbent product of claim 1 wherein the electric field is generated between an electric field source and a collecting means.

15. The disposable absorbent product of claim 14 wherein the electric field source is an electrostatic generator.

16. The disposable absorbent product of claim 14 wherein the collecting means is grounded.

17. The disposable absorbent product of claim 14 wherein the material responsive to an electric field is introduced into the electric field closer to the collecting means than to the electric field source.

18. The disposable absorbent product of claim 14 wherein the substrate is positioned on the collecting means, and the material responsive to an electric field is contacted directly with the substrate.

19. The disposable absorbent product of claim 14 wherein the material responsive to an electric field is contacted directly with the collecting means and subsequently transferred to a substrate.

20. The disposable absorbent product of claim 14 wherein the collecting means comprises a magnet.

21. The disposable absorbent product of claim 20 wherein the material responsive to an electric field is in a composition also comprising a magnetically responsive material.

22. The disposable absorbent product of claim 14 wherein the electric field source is at a voltage potential between about 2 to about 10 kilovolts per centimeter of space between the electric field source and the collecting means.

23. The disposable absorbent product of claim 14 wherein the electric field source and the collecting means have a current running between them of less than about 1 milliamp.

* * * * *